United States Patent [19]

Marhold et al.

[11] Patent Number: 4,533,777
[45] Date of Patent: Aug. 6, 1985

[54] PROCESS FOR THE PREPARATION OF AROMATIC TRIFLUOROMETHYL COMPOUNDS

[75] Inventors: Albrecht Marhold, Leverkusen; Erich Klauke, Odenthal, both of Fed. Rep. of Germany

[73] Assignee: Bayer Aktiengesllschaft, Leverkusen, Fed. Rep. of Germany

[21] Appl. No.: 65,776

[22] Filed: Aug. 13, 1979

[30] Foreign Application Priority Data

Aug. 28, 1978 [DE] Fed. Rep. of Germany ....... 2837499

[51] Int. Cl.$^3$ ............................................. C07C 17/32
[52] U.S. Cl. ..................................... 570/144; 568/56; 568/639
[58] Field of Search ......................... 260/651 F, 649 F; 570/144, 191, 194; 568/639, 56

[56] References Cited

U.S. PATENT DOCUMENTS

| | | | |
|---|---|---|---|
| 2,273,922 | 1/1961 | Benning et al. | 570/194 |
| 3,136,822 | 6/1964 | Frainier | 260/651 F |
| 4,155,940 | 5/1979 | Marhold et al. | 260/651 F |
| 4,207,266 | 6/1980 | Opie | 570/144 |

*Primary Examiner*—Charles F. Warren
*Assistant Examiner*—Joseph A. Boska

*Attorney, Agent, or Firm*—Sprung, Horn, Kramer & Woods

[57] ABSTRACT

A process for the preparation of an aromatic trifluoromethyl compound which comprises contacting an aromatic compound of the formula

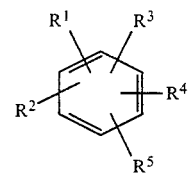

wherein $R^1$ denotes hydrogen, alkyl, aryl, aralkyl, aryloxy, arylthio, polyhalogenoalkoxy or polyhalogenoalkylthio and the aromatic substituents $R^1$ can in turn be substituted by halogen, alkyl, polyhalogenoalkyl, polyhalogenoalkoxy, polyhalogenoalkylthio, nitro, chlorocarbonyl or chlorosulfonyl, and $R^2$, $R^3$, $R^4$ and $R^5$ are independently hydrogen, halogen or alkyl and two adjacent radicals of the group $R^1$ to $R^5$ can conjointly form a three-membered to five-membered alkylene radical, with carbon tetrachloride and hydrogen fluoride at a temperature in the range of 50° C. to 140° C. Certain new aromatic trifluoromethyl compounds which can prepared by such a process are also disclosed.

6 Claims, No Drawings

PROCESS FOR THE PREPARATION OF AROMATIC TRIFLUOROMETHYL COMPOUNDS

The invention relates to a process for the preparation of aromatic trifluoromethyl compounds, and to new aromatic trifluoromethyl compounds.

It is known to prepare benzotrifluoride by fluorination of benzotrichloride with anhydrous hydrofluoric acid (Houben-Weyl, Methoden der organischen Chemie (Methods of organic Chemistry), volume V/3, page 121, Georg Thieme, Stuttgart 1962). This process is restricted to compounds which do not carry any further substituents which also undergo chlorination when chlorinating a methyl group. Thus, for example, 4-methyl-benzotrichloride is not obtainable by the said process. Furthermore, this process always involves two stages, since first a methyl group must be chlorinated to the trichloromethyl group and only then can the desired benzotrifluoride be prepared by fluorination.

A process has been found for the preparation of aromatic trifluoromethyl compounds, which is characterised in that an aromatic compound of the formula

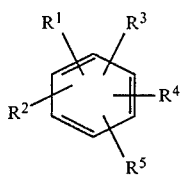
(I)

in which
  $R^1$ denotes hydrogen, alkyl, aryl, aralkyl, aryloxy, arylthio, polyhalogenoalkoxy or polyhalogenoalkylthio, and the aromatic substituents $R^1$ can in turn be substituted by halogen, alkyl, polyhalogenoalkyl, polyhalogenoalkoxy, polyhalogenoalkylthio, nitro, chlorocarbonyl or chlorosulfonyl and $R^2$, $R^3$, $R^4$ and $R^5$ are identical or different and denote hydrogen, halogen or alkyl, and
  two adjacent radicals from the group $R^1$ to $R^5$ can conjointly form a three-membered to five-membered alkylene radical,
is reacted with carbon tetrachloride and hydrogen fluoride in the temperature range of 50° to 140° C.

Halogen substituents ($R^2$ to $R^5$) are fluorine, chlorine or bromine.

Alkyl substituents ($R^1$ to $R^5$) can be those with 1 to 8 carbon atoms, for example methyl, ethyl, propyl, butyl, hexyl or octyl, preferably those with 1 to 4 carbon atoms, and particularly preferably methyl.

Aryl substituents ($R^1$) can be those with 6 to 12 carbon atoms, for example phenyl or diphenyl, preferably phenyl.

Aralkyl substituents ($R^1$) can be those with 1 or 2 carbon atoms in the aliphatic part and 6 to 12 carbon atoms in the aromatic part, for example benzyl, phenylethyl, diphenylmethyl or diphenylethyl, preferably benzyl.

Aryloxy substituents ($R^1$) can be those with 6 to 12 carbon atoms, for example phenyloxy or diphenyloxy, preferably phenyloxy.

Arylthio substituents ($R^1$) can be those with 6 to 12 carbon atoms, for example phenylthio or diphenylthio, preferably phenylthio.

Polyhalogenoalkoxy substituents ($R^1$) can be those with 1 to 4 carbon atoms, which carry fluorine, chlorine or bromine as halogen atoms, and in which the halogen atoms can be identical or different. Examples which may be mentioned are trifluoromethoxy, trichloromethoxy, tribromomethoxy, difluorochloromethoxy, difluorobromomethoxy, fluorodichloromethoxy, fluorodibromomethoxy, dibromochloromethoxy, bromodichloromethoxy, pentafluoroethoxy, pentachloroethoxy, pentabromoethoxy and α-difluoro-β-fluoro-β-chloro-ethoxy, the propoxy radicals containing identical or different halogens or the butoxy radicals containing identical or different halogens. The polyhalogenoalkoxy substituents with 1 to 2 carbon atoms are preferred, and the methoxy substituents containing identical or different halogens are especially preferred.

Polyhalogenoalkylthio substituents ($R^1$) can be those mentioned as polyhalogenoalkoxy substituents, but with a sulphur atom in place of the oxygen atom. They can have 1 to 4 carbon atoms, preferably 1 to 2 carbon atoms or very particularly preferably 1 carbon atom.

The aryl, aralkyl, aryloxy or arylthio substituents ($R^1$) can be substituted in their aromatic part by halogen, for example fluorine, chlorine or bromine, $C_1$–$C_4$-alkyl, for example methyl, ethyl, propyl or butyl, $C_1$–$C_4$-polyhalogenoalkyl, polyhalogenoalkoxy or polyhalogenoalkylthio, for example respectively, methyl, ethyl, propyl or butyl, methoxy, ethoxy, propoxy or butoxy, and methylthio, ethylthio, propylthio or butylthio, which contain identical or different halogens, or by nitro, chlorocarbonyl or chlorosulfonyl.

The alkyl substituents ($R^1$ to $R^5$) can, for their part, be substituted by halogenoalkyl groups.

Two adjacent radicals $R^1$ to $R^5$ can furthermore conjointly form a 3-membered to 5-membered alkylene radical, for example trimethylene, tetramethylene or pentamethylene.

The following may be mentioned as examples of compounds of the formula (I): benzene, fluorobenzene, chlorobenzene, bromobenzene, toluene, 2-chlorotoluene, 3-chlorotoluene, 4-chlorotoluene, 2,3-dichlorotoluene, 2,4-dichlorotoluene, 2,5-dichlorotoluene, 2,6-dichlorotoluene, 3,4-dichlorotoluene, 3,5-dichlorotoluene, the isomeric difluorotoluenes and dibromotoluenes, the three isomeric xylenes, 1-chloro-2,3-dimethylbenzene, 1-chloro-2,4-dimethylbenzene, 1-chloro-3,4-dimethylbenzene, 1-chloro-3,5-dimethylbenzene, ethylbenzene, isopropylbenzene, 2-chloro-ethylbenzene, 3- and 4-chloro-ethylbenzene, mesitylene, chloromesitylene, bromomesitylene, durene, chlorodurene, bromodurene, all the isomeric dichloro-dimethylbenzenes, diphenyl, alkyl-substituted or halogen-substituted diphenyls, alkyl-substituted or halogen-substituted diphenyl ethers, tetralin, chlorotetralin, diphenylmethane, pentafluoroethyl phenyl ether, pentachloroethyl phenyl ether, pentabromoethyl phenyl ether or α-difluoro-β-fluoro-62 -chloro-ethyl phenyl ether.

The process according to the invention is preferably carried out by conversion of an aromatic compound of the formula (II)

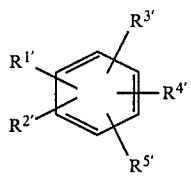 (II)

in which
R$^{1'}$ denotes hydrogen, alkyl, phenyl, phenyloxy or phenylthio,
R$^{2'}$, R$^{3'}$ and R$^{4'}$ are identical or different and represent hydrogen, halogen or methyl and
R$^{5'}$ denotes hydrogen or alkyl.

The process according to the invention is particularly preferentially carried out by conversion of an aromatic compound of the formula (III)

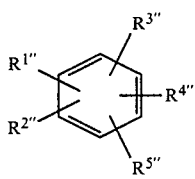 (III)

in which
R$^{1''}$ denotes hydrogen, methyl, phenyloxy or phenylthio,
R$^{2''}$, R$^{3''}$ and R$^{4''}$ are identical or different and represent hydrogen, halogen or methyl and
R$^{5''}$ is hydrogen or methyl.

For quantitative conversion of the aromatic compound (I), at least 1 mol of carbon tetrachloride and 3 mols of hydrogen fluoride are necessary. Hence such quantities of CCl$_4$ and HF are preferably used. The individual reactants can however also be employed in less than the stoichiometric amount, or in excess. In general, however, it is advisable to employ carbon tetrachloride or anhydrous hydrogen fluoride or both reactants in excess and, by doing so, to employ them as the solvent or diluent. In carrying out the process according to the invention, the sequence of addition of the individual reactants is immaterial.

The reaction of the process according to the invention is carried out in the temperature range of 50° to 140° C. Preferably, the temperature range of 60° to 130° C. is used, whilst the temperature range of 80° to 120° C. is particularly preferred.

To carry out the process according to the invention in the liquid phase, the use of excess pressure is necessary. The minimum pressure required is that which corresponds to hydrogen fluoride boiling at the selected working temperature. In general, a pressure of 5 to 30 bar is suitable. This pressure can for example be achieved as a result of the autogenous pressure of the reactants employed and the reactants formed. However, it is also possible to set up the selected pressure by means of compressed atmospheric air or by means of a compressed inert gas, for example nitrogen.

The reaction of the process according to the invention will be illustrated by the following equation, which relates to the example of the reaction of 1,4-dichloro-2,5-dimethylbenzene with carbon tetrachloride and hydrogen fluoride to give 2,5-dichloro-3,6-dimethylbenzotrifluoride:

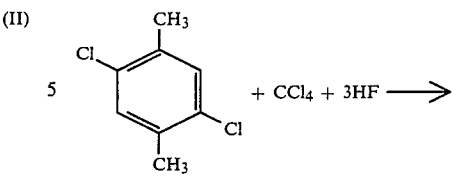

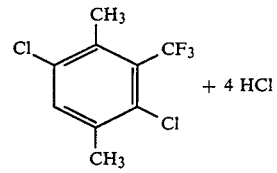

The process according to the invention can, for example, be carried out as follows:

Anhydrous liquid hydrogen fluoride is introduced, with cooling, into a stainless steel autoclave, and a solution of the aromatic compound (I) in carbon tetrachloride is added. A pressure of about 3 bar is then set up with nitrogen, and the content of the autoclave is brought to the desired reaction temperature whilst stirring. After a short time, the start of the reaction manifests itself through a rise in the pressure, due to the hydrogen chloride formed. This hydrogen chloride is continuously or discontinuously released via a brine-cooled reflux condenser fitted with a regulating valve. After the reaction has terminated, the excess hydrogen fluoride and the excess carbon tetrachloride are distilled off and the reaction product is isolated, for example by fractional distillation.

The aromatic trifluoromethyl compounds obtainable by the inventive process can be represented by the formula (IV)

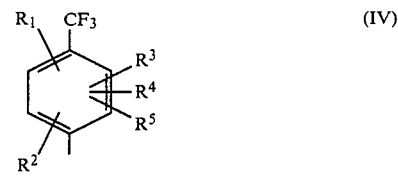 (IV)

in which R$^1$, R$^2$, R$^3$, R$^4$ and R$^5$ have the above identified meaning.

Many of the compounds of the formula (IV) are new.

The invention therefore also relates to new, aromatic trifluoromethyl compounds of the formula (V)

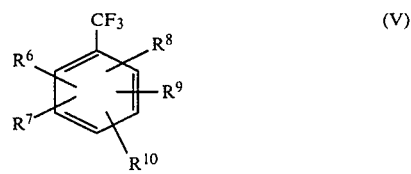 (V)

in which
R$^6$ represents methyl, C$_2$–C$_8$-alkyl, aryl, aralkyl, aryloxy, arylthio, polyhalogenoalkoxy or polyhalogenoalkylthio,
R$^7$, R$^8$ and R$^9$ are identical or different and denote hydrogen, halogen or alkyl,
R$^{10}$ denotes C$_2$–C$_8$-alkyl or, if R$^6$ has a meaning other than alkyl or aryloxy, or at least one of the radicals $R^7$ to $R^9$ is halogen or at least 2 are alkyl, also denotes hydrogen or methyl, and two adjacent radicals of the group $R^6$ to $R^{10}$ can conjointly form a three-membered to five-membered alkylene radical.

The same explanations and examples relate to the substituents $R^6$ to $R^{10}$ as to the substituents $R^1$ to $R^5$ in formula (I).

The invention preferentially relates to new aromatic trifluoromethyl compounds of the formula (VI)

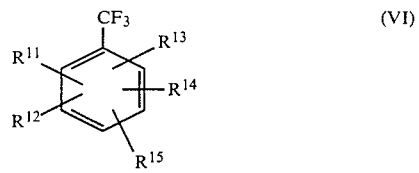

in which $R^{11}$ denotes methyl, $C_2$–$C_4$-alkyl, phenyl, phenyloxy or phenylthio, $R^{12}$, $R^{13}$ and $R^{14}$ are identical or different and represent hydrogen, halogen or methyl, and $R^{15}$ denotes $C_2$–$C_4$-alkyl or, if $R^{11}$ has a meaning other than methyl or phenyloxy, or at least one of the radicals $R^{12}$ to $R^{14}$ is halogen or at least two are methyl, also denotes hydrogen or methyl.

Fluorine, chlorine or bromine may be mentioned as examples of halogen ($R^{12}$ to $R^{14}$).

Ethyl, propyl or butyl may be mentioned as examples of $C_2$–$C_4$-alkyl ($R^{11}$, $R^{15}$).

The phenyl or phenyloxy substituent ($R^{11}$) can be substituted by halogen, for example fluorine, chlorine or bromine, by $C_1$–$C_4$-alkyl, for example methyl, ethyl, propyl or butyl, preferably methyl, or by $C_1$–$C_4$-polyhalogenoalkoxy or $C_1$–$C_4$-polyhalogenoalkylthio, or by nitro, chlorocarbonyl or chlorosulfonyl.

The invention further relates, very particularly preferentially, to the new aromatic trifluoromethyl compounds of the formula (VII)

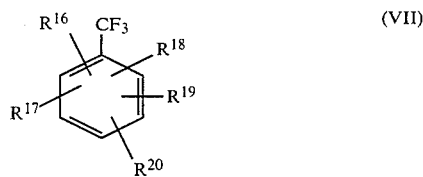

in which $R^{16}$, $R^{17}$ and $R^{18}$ are identical or different and represent methyl, fluorine, chlorine or bromine, and if $R^{16}$ and $R^{17}$ are other than chlorine, $R^{18}$ can also additionally be hydrogen, and $R^{19}$ and $R^{20}$ are identical or different and denote hydrogen or methyl.

Whilst the industrial synthesis of benzotrifluoride is carried out via the stages of chlorination of the methyl group and subsequent fluorination of the trifluoromethyl group, and whilst laboratory preparation of substituted benzotrifluorides may only be possible by means of multi-stage syntheses which may entail high losses, the process according to the invention permits the preparation of aromatic trifluoromethyl compounds in merely one reaction step.

It is surprising that the process according to the invention yields the end products according to the invention smoothly and in good yield, since it might have been expected that aromatic compounds would, in the presence of a chloroalkyl compound, such as carbon tetrachloride, and of a Friedel-Crafts catalyst undergo extensive, possibly uncontrollable, condensation or resinification reactions.

Thus it is for example known that benzene and carbon tetrachloride, in the presence of aluminum chloride as a Friedel-Crafts catalyst, give trityl chloride (Organikum, page 302, 8th edition, VEB-Verlag, Berlin 1968). The same publication also reports on the polyalkylation by polyhalogenated alkanes, so that the selective introduction of $CF_3$ groups into aromatics by the process according to the invention is surprising.

The benzotrifluorides obtainable by the process according to the invention are important intermediate products for dyestuffs, insecticides and herbicides. Thus, for example, 2-methyl-4-chlorobenzotrifluoride by nitration gives 2-methyl-3,5-dinitro-4-chloro-benzotrifluoride, which can be reacted with secondary amines to give N,N-disubstituted 2,6-dinitro-3-methyl-4-trifluoromethylanilines, which are active as growth regulators and herbicides (DE-OS (German Published Specification) No. 2,232,263 and DE-OS (German Published Specification) No. 2,241,408).

As another example, benzotrifluoride by nitration gives 3-nitrobenzotrifluoride which in turn by reduction gives 3-aminobenzotrifluoride. The latter can be reacted with phosgene to yield the 3-isocyanatobenzotrifluoride. In the subsequent reaction of the isocyanate with dimethylamine the 1-(3-trifluoromethylphenyl)-3-dimethyl-urea is obtained which is an important herbicide (DE-AS (German Examined Specification) No. 1206201).

The preparation of other active insecticides and herbicides, but also of other dyestuffs, which require aromatic trifluoromethyl compounds as intermediate products has hitherto failed because of the inadequate accessibility of suitable aromatic trifluoromethyl compounds.

A further characteristic, which represents an advance, of the present invention is that such aromatic trifluoromethyl compounds are made available.

EXAMPLE 1

1,500 g of anhydrous hydrogen fluoride, 860 g of 3-chlorotoluene and 2,500 g of carbon tetrachloride are initially introduced, at 10° C., into a VA autoclave equipped with a stirrer, reflux condenser and pressure-regulating valve. Nitrogen is then forced in to a pressure of 3 bar, and the mixture is heated to 102°–104° C. for 12 hours, whilst stirring. The hydrogen chloride formed is continuously released at 15.5 bar. After the end of the reaction, the excess hydrogen fluoride and the carbon tetrachloride are distilled off. The reaction product is distilled through a column and 290 g of 2-methyl-4-chlorobenzotrifluoride, boiling point$_{50}$: 83°–4° C., 85 g of an intermediate fraction and 922 g of 4-methyl-2-chlorobenzotrifluoride, boiling point$_{50}$: 91° C., $n_D^{20}$: 1.4600, are obtained.

EXAMPLE 2

900 ml of hydrogen fluoride, 1,200 ml of carbon tetrachloride and 300 g of 2-chlorotoluene are initially introduced at 0° C. into a VA autoclave. The mixture is kept at 107° to 110° C. for 6 hours, whilst stirring, and the hydrogen chloride formed is released at a rate corresponding to the maintainance of a pressure of about 25 bar. At the end of the reaction time, the autoclave is cooled, and the reaction content is worked up by distillation. 395 g of a mixture which, according to analysis by gas chromatography, consists of 25% of 2-chlorotoluene, 15.7% of 4-methyl-3-chloro-benzotrifluoride (boiling point$_{50}$: 80°-1° C.) and 59.1% of 3-methyl-2-chloro-benotrifluoride (boiling point$_{50}$: 93°-4° C.), are obtained. The reaction products are separated by fractional distillation.

EXAMPLE 3

A mixture of 1,500 ml of hydrogen fluoride, 400 g of mesitylene and 1,500 ml of carbon tetrachloride are heated to 92°-3° C. for 18 hours and the hydrogen chloride is released at 11.5 bar. The hydrogen fluoride is then distilled off and the residue is fractionated. 385 g of 2,4,6-trimethylbenzotrifluoride, boiling point$_{15}$: 55°-8° C., $n_D^{20}$: 1.4550, are obtained, corresponding to a yield of 61% of theory.

EXAMPLE 4

300 ml of hydrogen fluoride, 900 ml of carbon tetrachloride and 100 g of toluene are initially introduced at 10° C. into an autoclave, and are then heated to 106° C. for 10 hours, whilst stirring, the hydrogen chloride being released at 16.4 bar. After working up analogously to Example 1, 102 g of reaction product are obtained, consisting of 10.6% of 3-methylbenzotrifluoride (boiling point: 131° C., $n_D^{20}$: 1.4258, 48% of 2-methylbenzotrifluoride (boiling point: 128° to 129° C., $n_D^{20}$: 1.4322) and 41.4% of 4-methylbenzotrifluoride (boiling point: 134° C., $n_D^{20}$: 1.4255). The three methyl-benzotrifluorides can be separated by distillation through a column.

EXAMPLE 5

500 ml of hydrogen fluoride, 600 ml of carbon tetrachloride and 140 g of 2,5-dimethyl-chlorobenzene are reacted for 10 hours at 101°-3° C., similarly to Example 1. Distillation gives 191 g of 2,5-dimethyl-4-chlorobenzotrifluoride, boiling point$_{15}$: 81°-83° C., $n_D^{20}$: 1.4715.

EXAMPLE 6

400 ml of hydrogen fluoride, 500 ml of carbon tetrachloride and 100 g of 2,5-dichloro-p-xylene are reacted, analogously to Example 1, for 10 hours at 100° C. and a pressure of 14.5 bar. 90 g of 2,5-dimethyl-3,6-dichlorobenzotrifluoride, melting point: 62° to 63° C., are obtained.

EXAMPLE 7

500 ml of hydrogen fluoride, 600 ml of carbon tetrachloride and 140 g of 3,4-dichlorotoluene are reacted at 110° to 115° C. and 18.5 to 19.5 bar pressure. 151 g of a stubstance containing, in addition to 79.1% by weight of 3,4-dichlorotoluene, 20.2% by weight of 2-methyl-4,5-dichloro-benzotrifluoride, are obtained, corresponding to 74% of the theoretical yield, relative to 3,4-dichlorotoluene converted.

EXAMPLE 8

If 400 ml of hydrogen fluoride, 170 g of diphenyl ether and 400 ml of carbon tetrachloride are reacted for 6 hours at 112° to 115° C., 20 g of 4-trifluoromethyl-diphenyl ether, boiling point$_{14}$: 125°-127° C., are obtained.

EXAMPLE 9

200 g of pentamethylbenzene, 750 ml of carbon tetrachloride and 500 g of anhydrous hydrogen fluoride are heated for 10 hours to 80°-82° C. and the hydrogen chloride formed is released at 14 bar. Working up of the reaction mixture by distillation gives 112 g of pentamethylbenzotrifluoride, boiling point$_{14}$: 108° to 112° C. in addition to 35 g of starting material.

EXAMPLE 10

200 g of bromobenzene, 500 ml of carbon tetrachloride and 500 g of anhydrous hydrogen fluoride are reacted, analogously to Example 1, in 10 hours at 108° to 110° C. and 18 bar. 212 g of reaction product of a boiling range corresponding to a boiling point$_{37}$: 64° to 74° C. are obtained: this product consists of 61.1% by weight of bromobenzene, 14.3% by weight of 4-bromobenzotrifluoride and 23.5% by weight of 2-bromobenzotrifluoride. The weight ratios in the reaction product were determined by analysis by gas chromatography. The mixture can be separated by distillation through a column. The yield of the two isomeric bromobenzotrifluorides is 85% of the theoretical yield, relative to bromobenzene converted.

EXAMPLE 11

500 g of anhydrous hydrogen fluoride, 600 ml of carbon tetrachloride and 110 g of 3-fluorotoluene are reacted analogously to Example 1, in 8 hours at 105° C. and 16.7 bar. 132 g of the reaction mixture which according to analysis by gas chromatography contains 64.4% by weight of 3-methyl-4-fluoro-benzotrifluoride in addition to 33.7% by weight of 3-fluorotoluene are obtained. The yield of 3-methyl-4-fluorobenzotrifluoride is 87% of the theoretical yield, relative to 3-fluorotoluene consumed.

EXAMPLE 12

400 g of anhydrous hydrogenfluoride, 100 g of 4-nitro-2'-methyl-diphenyl ether and 700 ml of carbon tetrachloride are reacted, analogously to Example 1, in 6 hours at 110° C. and 18 bar. 118 g of 4-nitro-2'-trifluoromethyl-6'-methyl-diphenyl ether are obtained by destillation. Boiling point $_{0,6}$: 150°-155° C., $n_D^{20}$: 1.5762.

EXAMPLE 13

A mixture of 400 g of anhydrous hydrogen fluoride, 120 g of 3,3'-dimethyl-diphenylether and 600 ml of carbon tetrachloride are heated in 6 hours at 85°-88° C. and 12 bar. The developed hydrogen chloride is released continuously. After working up by destillation 53 g of 2-trifluoromethyl-5,3'-dimethyl-diphenyl ether are obtained, boiling point $_{0,1}$: 98° to 100° C.

EXAMPLE 14

In a stainless steel autoclave are placed 250 ml of anhydrous hydrogen fluoride at 10° C. and a mixture of 50 g of benzene in 300 ml of carbon tetrachloride is added. Nitrogen is then forced in to a pressure of 3 bar, and the mixture is heated to 100° C. for 5 hours. The hydrogen chloride formed is continuously released at 15 bar. The superfluous hydrogen fluoride is destilled off from the reaction mixture at a temperature of up to 50° C. The remaining solution is washed with water and dried with sodium sulphate. This solution obtained (387 g) is analysed by gas chromatography. The solution contains 84,4% by weight carbon tetrachloride and 13,43% by weight trifluoromethyl benzene which corresponds to a yield of 52 g of trifluoromethyl benzene.

EXAMPLE 15

500 ml of anhydrous hydrogen fluoride are reacted with 700 ml of carbon tetrachloride and 100 g of 2,4-dimethyl-phenyl trifluoromethyl thioether, analogously to Example 1, in 9 hours at 105° C. and a pressure of 15,3 bar. After working up by destillation 106 g of a reaction mixture are obtained with a boiling point $_{14}$ of 74°–79° C. and a $n_D{}^{20}$ of 1.4700 which contains according to gas chromatographic analysis 79,4% by weight starting material and 20,1% by weight trifluoromethyl-substituted 2,4-dimethyl-phenyl-trifluoromethyl thioether.

EXAMPLE 16

A mixture of 500 ml of anhydrous nitrogen fluoride, 100 g of 4-diphenyl-carbon acid chloride and 500 ml of carbon tetrachloride are heated for 6 hours at a pressure of 19.5 bar at 110° C. The working up by destillation yields 74 g of 4′-trifluoromethyl-4-diphenyl-carbon acid fluoride, boiling point$_{0,2}$: 122°–125° C., melting point 93°–95° C.

EXAMPLE 17

400 g of anhydrous hydrogen fluoride, 150 g of 4-nitro-3′-methyl-diphenylether and 800 ml of carbon tetrachloride are heated for 6 hours at 110° C. and 18 bar, analogously to Example 1. After working up by destillation 140 g of a mixture of the boiling point $_{0,1}$: 110°–130° C. are obtained from which 4-nitro-4′-trifluoromethyl-3′-methyl-diphenyl ether crystallises, melting point 66°–68° C.

EXAMPLE 18

From a mixture of 100 g of 4-nitrodiphenyl, 500 ml of carbon tetrachloride and 400 ml of anhydrous hydrogen fluoride are obtained after 8 hours at 110° C. and 17–19 bar, analogously to Example 1, 108 g of 4-trifluoromethyl-4′-nitrodiphenyl. Melting point: 112°–114° C. after recrystallisation from methanol.

EXAMPLE 19 TO 22

The examples of the following table were carried out analogously to example 1, but the 3-chlorotoluene was replaced by the compounds listed in the table.

| | | Table of examples 19 to 22 | |
|---|---|---|---|
| No. | starting material | reaction compound | physical data |
| 19 | CH₃, Cl, Cl (benzene) | CH₃, Cl, Cl, CF₃ (benzene) | boil. p.$_{51}$: 123° C.<br>$n_D{}^{20}$: 1.4960 |
| 20 | CH₂—CH₃ (benzene) | CH₂—CH₃, CF₃ (benzene) + CH₂—CH₃, CF₃ (benzene)<br>main product | main product:<br>boil. p.$_{150}$: 88–90° C.<br>$n_D{}^{20}$: 1.4508 |
| 21 | CH₃, CH₃, CH₃, Cl (benzene) | CH₃, CF₃, CH₃, CH₃, Cl (benzene) | boil. p.$_{74}$: 136° C.<br>$n_D{}^{20}$: 1.4868 |
| 22 | CH₃, CH₃, CH₃, CH₃ (benzene) | CF₃, CH₃, CH₃, CH₃, CH₃ (benzene) | boil. p.$_{14}$: 75–76° C. |

What is claimed is:

1. A method for adding a trifluoromethyl group to the ring of a benzene ring compound which comprises contacting an aromatic compound of the formula

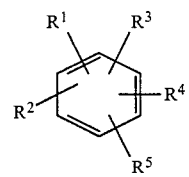

wherein
R$^1$ denotes hydrogen, alkyl, phenyl, phenyloxy or phenylthio,
R$^2$, R$^3$ and R$^4$, are identical or different and denote hydrogen, halogen, or methyl and
R$^5$ is hydrogen or alkyl
and 2 adjacent radicals of the group R$^1$ through R$^5$ being able to jointly form a 3- to 5-membered alkylene radical with carbon tetrachloride and hydrogen fluoride at a temperature in the range of 50° to 140° C., the reaction mixture consisting essentially of said aromatic compound, said carbon tetrachloride, and said hydrogen fluoride.

2. A method according to claim 1, wherein at least 1 mol carbon tetrachloride and at least 3 mols hydrogen fluoride are employed per mol of said aromatic compound.

3. A method according to claim 1, wherein the reaction is effected at 60°–130° C.

4. A method according to claim 1, wherein the reaction is effected in the liquid phase at a pressure of 5 to 30 bars.

5. A method according to claim 1, wherein the reaction is effected under the pressures of the reaction components which exist at the temperature of the reaction.

6. A process for adding a trifluoromethyl group to the ring of a benzene ring compound which comprises contacting an aromatic compound of the formula

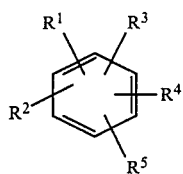

wherein
- $R^1$ denotes hydrogen, methyl, phenyloxy or phenylthio,
- $R^2$, $R^3$ and $R^4$, are identical or different and denote hydrogen, halogen or methyl and
- $R^5$ is hydrogen or methyl and 2 adjacent radicals of the group $R^1$ through $R^5$ being able to jointly form a 3- to 5-membered alkylene radical with carbon tetrachloride and hydrogen fluoride at a temperature in the range of 50° to 140° C., the reaction mixture consisting essentially of said aromatic compound, said carbon tetrachloride, and said hydrogen fluoride.

* * * * *